United States Patent [19]

Julia et al.

[11] Patent Number: 4,670,577

[45] Date of Patent: Jun. 2, 1987

[54] NOVEL PROCESS

[75] Inventors: Marc Julia; Thérèse Cuvigny, both of Paris, France

[73] Assignee: Roussel Uclaf, Paris, France

[21] Appl. No.: 583,155

[22] Filed: Feb. 24, 1984

[30] Foreign Application Priority Data

Mar. 1, 1983 [FR]  France ............................. 83 03328

[51] Int. Cl.[4] .................. C07C 49/203; C07C 69/533; C07C 120/00; C07C 121/30
[52] U.S. Cl. .................................... 558/378; 558/371; 560/17; 560/51; 560/145; 560/150; 560/174; 560/190; 560/205; 568/28; 568/312; 568/388; 568/31
[58] Field of Search ...................... 260/465.4, 465.8 R; 560/190, 174, 17, 51, 145, 150, 205; 568/317, 388, 28, 312, 31; 558/371, 378

[56] References Cited

U.S. PATENT DOCUMENTS 4,362,670  12/1982  Woo ................................. 260/465 R

OTHER PUBLICATIONS

Cuvigny, et al.; Journal of Organometallic Chemistry, 285, (1985), pp. 395–413.
Miller, et al.; J. Chem. Soc.—Perkin I, (1973), pp. 603–606.
Billington; Chem. Soc. Rev., 1985, 14; pp. 93–120.
Baker; Chem. and Ind., 18, Oct. 1980, pp. 816–823.
Trost, et al.; J. Org. Chem., 40, (1975), pp. 3617–3619.
Trost, et al.; J. Org. Chem.; 41, (1976), pp. 3215–3216.

Primary Examiner—Joseph P. Brust
Attorney, Agent, or Firm—Bierman & Muserlian

[57] ABSTRACT

A novel process for the preparation of pent-4-enoic acids of the formula

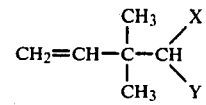

wherein X is selected from the group consisting of hydrogen, cyano and alkoxycarbonyl of 2 to 5 carbon atoms and Y is selected from the group consisting of hydrogen, cyano, alkoxycarbonyl 2 to 5 carbon atoms, acyl of an organic carboxylic acid of 2 to 7 carbon atoms, alkylsulfonyl of 1 to 4 carbon atoms and arylsulfonyl of 6 to 7 carbon atoms with the proviso that X and Y are not both hydrogen comprising reacting a compound of the formula

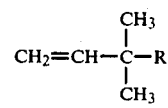

wherein R is selected from the group consisting of acyloxy of an organic carboxylic acid of 1 to 7 carbon atoms, alkylsulfonyl of 1 to 4 carbon atoms and arylsulfonyl of 6 to 7 carbon atoms with an anion derivative of a compound of the formula

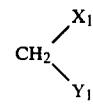

wherein $X_1$ and $Y_1$ have the above definition for X and Y, respectively, except hydrogen in the presence of a palladium compound or nickel (o) complex and optionally a catalytic quantity of a ligand to obtain a compound of the formula

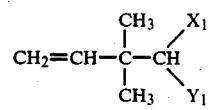

wherein $X_1$ and $Y_1$ have the above definition and optionally subjecting the latter to a decarbalkoxylation when $X_1$ or $Y_1$ is alkoxycarbonyl or to a reduction when $X_1$ is arylsulfonyl to obtain the corresponding compound of formula I.

15 Claims, No Drawings

NOVEL PROCESS

STATE OF THE ART

French Pat. No. 2,341,553 describes the preparation of compounds of formula I by a very different process. U.S. Pat. No. 4,362,670 describes allylation using palladium catalysts and Tetrahedron, Vol. 33 (1977), p. 2615-2649 describes organic synthesis using organic palladium catalysts. None of the references relate to nickel catalysts for the reaction of the invention.

THE INVENTION

The novel process of the invention for the preparation of pent-4-enoic acids of the formula

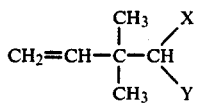

wherein X is selected from the group consisting of hydrogen, cyano and alkoxycarbonyl of 2 to 5 carbon atoms and Y is selected from the group consisting of hydrogen, cyano, alkoxycarbonyl of 2 to 5 carbon atoms, acyl of an organic carboxylic acid of 2 to 7 carbon atoms, alkylsulfonyl of 1 to 4 carbon atoms and arylsulfonyl of 6 to 7 carbon atoms with the proviso that X and Y are not both hydrogen comprises reacting a compound of the formula

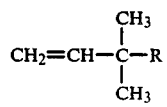

wherein R is selected from the group consisting of acyloxy of an organic carboxylic acid of 1 to 7 carbon atoms, alkylsulfonyl of 1 to 4 carbon atoms and arylsulfonyl of 6 to 7 carbon atoms with an anion derivative of a compound of the formula

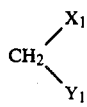

wherein $X_1$ and $Y_1$ have the above definition for X and Y, respectively, except hydrogen in the presence of a palladium compound or nickel (o) complex and optionally a catalytic quantity of a ligand to obtain a compound of the formula

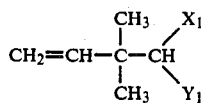

wherein $X_1$ and $Y_1$ have the above definition and optionally subjecting the latter to a decarbalkoxylation when $X_1$ or $Y_1$ is alkoxycarbonyl or to a reduction when $X_1$ is arylsulfonyl to obtain the corresponding compound of formula I.

When X or Y is an alkoxycarbonyl of 2 to 5 carbon atoms, they are preferably a methoxycarbonyl or ethoxycarbonyl. When Y is an acyl of 2 to 7 carbon atoms, it is preferably acetyl, propionyl or benzoyl. When Y or R is alkylsulfonyl, the alkyl is preferably methyl or ethyl. When Y or R is arylsulfonyl, it is preferably a phenylsulfonyl or a p-toluene sulfonyl. When R is acyloxy, it is preferably acetyloxy, propionyloxy, butyryloxy or benzoyloxy.

When reaction of the compound of formula II with the compound of formula III is carried out in an organic solvent, it is, notably, an ether, more particularly tetrahydrofuran or ethyl ether, dimethylsulfoxide or dimethylformamide. The anion derivative of a compound of formula III results from the derivative obtained by action of a basic agent such as an alkali metal hydride, an alkali metal alcoholate or an anhydrous alkali metal hydroxide, on the compound of formula III. This anion is preferably obtained from the derivative combined with sodium which in turn is obtained by reaction with sodium hydride.

The invention has particularly as its subject a process as previously defined, characterized in that a compound of formula III is used in which $Y_1$ is alkoxycarbonyl of 2 to 5 carbon atoms or cyano, and more particularly a process characterized in that of compound of formula III is used in which $X_1$ is cyano.

The invention has preferably as its subject a process as previously defined, characterized in that a palladium II complex is used and, more particularly, the palladium II complex is bis-($\eta_3$-allyl)-di-$\mu$-chlorodipalladium II or a palladium (o) complex is used, preferably tetrakis(triphenyl phosphine)palladium or di-(1,2-bis diphenyl phosphine ethane)palladium.

The invention also preferably relates to a process using a nickel (o) complex, especially a nickel complex prepared in situ by reduction of a nickel (II) complex which is more particularly, a complex formed by nickel dichloride with a compound chosen from the group consisting of triphenyl phosphine, tributyl phosphine, tri-isopropyl phosphine, diphenyl phosphinoethane, diphenyl phosphinopropane, diphenyl phosphinobutane and diphenyl phosphinohexane. The reducing agent for the nickel (II) complex is preferably magnesium isopropyl chloride.

In a preferred mode of the process of the invention using a palladium complex, the operation is carried out in the presence of a ligand which is preferably chosen from the group consisting of triphenyl phosphine, diphenyl phosphino-ethane, hexamethylphosphortriamide, triethyl phosphite, triphenyl phosphite and hydroquinone.

Decarbalkoxylation of the compound of formula $I_A$ is effected by heating in an organic solvent, preferably dimethylsulfoxide in the presence of water and, if applicable, of an alkali metal salt such as sodium chloride, potassium iodide or sodium cyanide or an organic base. The reduction of the compound of formula $I_A$ is effected by action of a metallic amalgam such as sodium or aluminum amalgam and the reaction is carried out in a lower alkanol such as methanol or ethanol.

The derivatives of pent-4-enoic acid of formula I are intermediates useful for the preparation of derivatives of 2,4-dimethyl-cyclopropane carboxylic acids substituted with a dihalovinyl group which derivatives are themselves well-known intermediates for the preparation of esters possessing pesticidal, especially insecticidal and acaricidal, properties. The cyclization of the derivatives of formula I into derivatives of 2,2-dimethyl-cyclopropane-carboxylic acids has been described in French Pat. No. 2,301,510, No. 2,318,143, No.

2,318,144, No. 2,351,943, as well as Belgian Pat. No. 847,865.

The process of the invention has with respect to the known processes to prepare the derivatives of formula I, the advantage of leading, in the most two stages, to these derivatives with remarkable yields and by using easily obtainable and inexpensive starting materials. Moreover, the process has the advantage, essentially in the case of compounds of formula III wherein $X_1$ is cyano and $Y_1$ is alkoxycarbonyl, of leading very selectively to the desired isomer leading to the substitution of the most substituted carbon of the molecule.

In the following examples, there are described several preferred embodiments to illustrate the invention. However, it should be understood that the invention is not intended to be limited to the specific embodiments.

EXAMPLE 1

Ethyl 2-cyano-3,3-dimethyl-pent-4-en-1-oate (use of palladium complex 9.2 mg of bis-($\eta_3$-allyl)-di-$\mu$-chlorodipalladium II and 26.2 mg of triphenylphosphine were mixed under inert gas at room temperature over a period of 10 minutes with 3 ml of tetrahydrofuran. Next, a solution of 512 mg of 3-acetoxy-3-methyl-but-1-ene in 3 ml of tetrahydrofuran was added followed by a suspension of ethyl cyanacetate and sodium (prepared starting with 791 mg of ethyl cyanacetate and 262 mg of a 55% dispersion of sodium hydride in oil in 18 ml of tetrahydrofuran). The mixture was stirred at room temperature under inert gas for 72 hours and then water was added thereto.

The mixture was extracted with ether and the decanted organic phase was dried and evaporated to dryness under reduced pressure. The residue was chromatographed over silica gel and eluted with a 1—1 petroleum ether-ether mixture to obtain 713 mg of ethyl 2-cyano-3,3-dimethyl-pent-4-en-1-oate with a boiling point of 122°–126° C. at 20 mm Hg consisting of 93% of the desired isomer and 7% of ethyl 2-cyano-5-methyl-hex-4-en-1-oate.

EXAMPLE 2

3,3-dimethyl-pent-4-en-nitrile

A mixture of 2.7 g of the product of Example 1, 0.3 g of sodium chloride, 0.6 g of water and 10 ml of dimethylsulfoxide was heated at 160° C. for 3 hours and was cooled and poured into water. The mixture was extracted with ether and the organic phase was dried and evaporated to dryness under reduced pressure to obtain 1.34 g of 3,3-dimethyl-pent-4-en-nitrile with a boiling point of 58° C. at 20 mm Hg.

EXAMPLE 3

Ethyl 2-cyano-3,3-dimethyl-pent-4-en-1-oate

A mixture of 131 mg of dichloro(bis triphenylphosphine)nickel II, 1.5 ml of tetrahydrofuran and 372 $\mu$l of a 1.08N solution of magnesium isopropyl chloride in ether was stirred at room temperature for 10 minutes and then a solution of 128 mg of 3-acetoxy-3-methyl-but-1-ene in 2 ml of tetrahydrofuran was added thereto followed by addition of a suspension of 248 mg of ethyl cyanoacetate, 88 mg of a 55% dispersion of sodium hydride in oil and 6 ml of tetrahydrofuran. The mixture was stirred at room temperature for 48 hours and a solution of ammonium chloride was added thereto. The mixture was extracted with ether and the decanted organic phase was dried and evaporated to dryness under reduced pressure. The residue was chromatographed over silica gel and eluted with a 1—1 ether-petroleum ether mixture to obtain 126 mg of ethyl 2-cyano-3,3-dimethyl-pent-4-en-1-oate containing 95% of the desired isomer and 5% of ethyl 2-cyano-5-methyl-hex-4-en-1-oate.

EXAMPLES 4 TO 33

Using the procedure of the foregoing examples, 3-acetoxy-but-1-ene (compound A) or 3-p-tolylsulfonyl-3-methyl-but-1-ene (compound B) were reacted under the conditions of the following Tables with the yields reported therein.

| Example | Comp. II | Compound III | Catalyst (note 1) (% molar) | Ligand (note 2) (% molar) | Solvent | Temperature | Reaction time | Yield | % of isomer I obtained |
|---|---|---|---|---|---|---|---|---|---|
| 4 | A | CH2(COOEt)2 | Pd(Tpp)4 (5) | TPP (20) | Tetrahydrofuran | Reflux | 36 h. | 68% | 73% |
| 5 | " | CH2(COOMe)2 | " | " | Tetrahydrofuran | " | " | 80% | 80% |
| 6 | " | CH2(COMe)(COOEt) | " | " | Tetrahydrofuran | " | " | 88% | 55% |
| 7 | " | CH2(CN)(COOEt) | " | " | Tetrahydrofuran | " | " | 100% | 86% |
| 8 | " | CH2(CN)(COOMe) | Pd(TPP)4 (2,5) | TPP (8) | Tetrahydrofuran | " | " | 79% | 92% |

-continued

| Example | Comp. II | Compound III | Catalyst (note 1) (% molar) | Ligand (note 2) (% molar) | Solvent | Temperature | Reaction time | Yield | % of isomer I obtained |
|---|---|---|---|---|---|---|---|---|---|
| 9 | " | CH$_2$(CN)(COOEt) | ($\eta_3$-C$_3$H$_5$)$_2$Pd$_2$Cl$_2$ (2,5) | P(OEt)$_3$ (10) | Tetrahydrofuran | " | " | 66% | 70% |
| 10 | " | " | Pd(DPPE)$_2$ (5) | DPPE (5) | Tetrahydrofuran | " | " | 78% | 73% |
| 11 | " | CH$_2$(CN)(CN) | Pd(TPP)$_4$ (5) | TPP (10) | Tetrahydrofuran | " | " | 98% | 95% |
| 12 | " | " | Pd(DPPE)$_2$ (5) | DPPE (5) | Tetrahydrofuran | " | " | 96% | 79% |
| 13 | " | CH$_2$(COOEt)(CN) | ($\eta^3$-C$_3$H$_5$)$_2$Pd$_2$Cl$_2$ (5) | TPP (5) HQ (10) | Tetrahydrofuran | 20° C. | 48 h. | 90% | 89% |
| 14 | " | " | ($\eta_3$C$_3$H$_5$)$_2$Pd$_2$Cl$_2$ (5) | TPP (10) | Tetrahydrofuran | 45° C. | 36 h. | 90% | 88% |
| 15 | " | " | " | TPP (5) | Tetrahydrofuran | 20° C. | 72 h. | 82% | 94% |
| 16 | " | " | ($\eta_3$C$_3$H$_5$)$_2$Pd$_2$Cl$_2$ (1,25) | TPP (2,5) | Tetrahydrofuran | " | " | 98,5% | 93% |
| 17 | B | CH$_2$(COOEt)(COOEt) | Pd(TPP)$_4$ (5) | TPP (20) | Tetrahydrofuran | Reflux | 36 h. | 88% | 77% |
| 18 | " | " | " | HMPT (50) | Tetrahydrofuran | " | " | 100% | 74% |
| 19 | " | " | ($\eta^3$C$_3$H$_5$)$_2$Pd$_2$Cl$_2$ (2,5) | TPP (15) | Tetrahydrofuran | " | " | 89% | 72% |
| 20 | " | CH$_2$(COOEt)(CN) | Pd(TPP)$_4$ (5) | TPP (20) | Tetrahydrofuran | " | " | 93% | 89% |
| 21 | A | CH$_2$(COOEt)(COOEt) | NiCl$_2$(TPP)$_2$ (20) | iPrMgCl | THF | 20° C. | " | 41% | 65% |
| 22 | " | CH$_2$(CN)(COOEt) | " | " | " | " | 48 h. | 70% | 95% |
| 23 | " | " | NiCl$_2$(DPPB) (5) | " | " | 45° C. | 24 h. | 89% | 80% |
| 24 | " | " | " | " | " | 35° C. | 36 h. | 48% | 90% |
| 25 | " | " | " | " | DMSO/THF (5/3) | 45° C. | " | 69% | 95% |
| 26 | " | " | NiCl$_2$(TPP) (20) | Zn | THF | " | " | 58% | 96% |
| 27 | " | CH$_2$(COOEt)(COOEt) | NiCl$_2$(TBP) (5) | iPrMgCl | THF | 65° C. | " | 30% | 65% |
| 28 | " | " | NiCl$_2$(DPPH) (5) | " | " | " | " | 55% | 71% |

-continued

| Example | Comp. II | Compound III | Catalyst (note 1) (% molar) | Ligand (note 2) (% molar) | Solvent | Temperature | Reaction time | Yield | % of isomer I obtained |
|---|---|---|---|---|---|---|---|---|---|
| 29 | " | 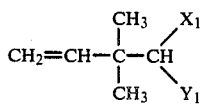 | NiCl$_2$(TBP) (20) | | " | " | Reflux | 24 h. | 68% | 82% |
| 30 | " | " | NiCl$_2$(TiP$_2$P) (20) | | " | " | " | " | 34% | 95% |
| 31 | " | " | NiCl$_2$(DPPP) (5) | | " | " | " | " | 80% | 60% |
| 32 | " | " | NiCl$_2$(DPPH) (5) | | " | " | " | " | 83% | 59% |
| 33 | B | " | NiCl$_2$(DPPE) (5) | | " | " | " | " | 68% | 52% |

(1) (2) TPP = triphenyl phosphine;
DPPB = diphenyl phosphinobutane;
TBP = tributyl phosphine;
DPPH = diphenyl phosphinohexane;
TiP,P = triisopropyl phosphine;
DPPP = diphenyl phosphinopropane;
DPPE = diphenyl phosphinoethane;
HQ = hydroquinone;
HMPT = hexamethyl phosphotriamide.

The molar percentages indicated are with regard to compound A or to compound B and in the case of a Pd (II) catalyst, they are expressed in atoms of Pd in relation to moles of A or B.

Various modifications of the process of the invention may be made without departing from the spirit or scope thereof and it should be understood that the invention is intended to be limited only as defined in the appended claims.

What we claim is:

1. A process for the preparation of pent-4-enoic acids of the formula

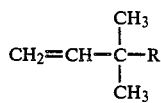

wherein $X_1$ is selected from the group consisting of cyano and alkoxycarbonyl of 2 to 5 carbon atoms and $Y_1$ is selected from the group consisting of cyano, alkoxycarbonyl of 2 to 5 carbon atoms, acyl of an organic carboxylic acid of 2 to 7 carbon atoms, alkylsulfonyl of 1 to 4 carbon atoms and carbocyclic arylsulfonyl of 6 to 7 carbon atoms comprising reacting in the liquid phase a compound of the formula $$CH_2=CH-\underset{\underset{CH_3}{|}}{\overset{\overset{CH_3}{|}}{C}}-R \quad\quad II$$

wherein R is selected from the group consisting of acyloxy of an organic carboxylic acid of 1 to 7 carbon atoms, alkylsulfonyl of 1 to 4 carbon atoms and carbocyclic arylsulfonyl of 6 to 7 carbon atoms with an alkali metal anion derivative of a compound of the formula

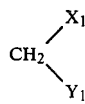

wherein $X_1$ and $Y_1$ have the above definition in the presence of a palladium complex or nickel (o) complex and optionally a catalytic quantity of a ligand to obtain a compound of the formula

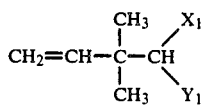

wherein $X_1$ and $Y_1$ have the above definition.

2. The process of claim 1 wherein $Y_1$ is alkoxycarbonyl of 2 to 5 carbon atoms or —CN.

3. The process of claim 1 wherein $X_1$ is —CN.

4. The process of claim 1 wherein a palladium (II) complex is used.

5. The process of claim 4 wherein the complex is bis($\eta_3$-allyl)-di-μ-chloro-dipalladium (II).

6. The process of claim 1 wherein a palladium (o) complex is used.

7. The process of claim 6 wherein the complex is tetrakis-(triphenylphosphine)-palladium.

8. The process of claim 6 wherein the complex is di-(1,2-bis-diphenylphosphine-ethane)-palladium.

9. The process of claim 1 wherein a nickel (o) complex is used.

10. The process of claim 9 wherein the complex is formed in situ by reduction of a nickel (II) complex.

11. The process of claim 10 wherein the complex is formed by reaction of nickel dichloride with a compound selected from the group consisting of triphenyl phosphine, tributyl phosphine, triisopropyl phosphine, diphenyl phosphino-ethane, diphenylphosphino propane, diphenyl-phosphino-butane and diphenyl phosphinohexane.

12. The process of claim 1 wherein the ligand is selected from the group consisting of triphenyl phosphine, diphenyl phosphinoethane, hexamethyl phosphotriamide, triethyl phosphite and triphenyl phosphite, hydroquinone.

13. The further process of claim 1 wherein one of $X_1$ or $Y_1$ is alkoxycarbonyl and the compound of formula I is subjected to a decarbalkoxylation.

14. The further process of claim 1 wherein $Y_1$ is arylsulfonyl and the compound of formula I is subjected to reaction with a reducing agent to obtain a compound wherein $Y_1$ is hydrogen.

15. The process of claim 10 wherein the reducing agent is magnesium isopropyl chloride.

* * * * *